US00PP22712P2

(12) United States Plant Patent
Egger

(10) Patent No.: US PP22,712 P2
(45) Date of Patent: May 1, 2012

(54) ***TIARELLA* PLANT NAMED 'OREGON TRAIL'**

(50) Latin Name: *Tiarella spp.*
Varietal Denomination: Oregon Trail

(75) Inventor: Janet Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 7 days.

(21) Appl. No.: 12/927,575

(22) Filed: Nov. 17, 2010

(51) Int. Cl.
*A01H 5/00* (2006.01)

(52) U.S. Cl. ..... Plt./486

(58) Field of Classification Search ..... Plt./486
See application file for complete search history.

*Primary Examiner* — Susan McCormick Ewoldt
(74) *Attorney, Agent, or Firm* — Jondle & Associates, P.C.

(57) ABSTRACT

A new and distinct cultivar of *Tiarella* plant characterized by medium size, palmately-lobed leaves, with the terminal lobe the longest, an extremely good trailing habit, low inflorescence number for a cleaner look, distinct, dark brown markings following the veins, and excellent vigor.

1 Drawing Sheet

Botanical denomination: *Tiarella* spp.
Variety designation: 'Oregon Trail'.
Cross Reference to siblings: *Tiarella* 'Cascade Creeper' (U.S. Plant Pat. No. 21,925) and *Tiarella* 'Happy Trails' (U.S. Plant Pat. No. 21,933).

BACKGROUND OF THE INVENTION

The present invention relates to a new and distinct cultivar of a hardy herbaceous perennial of the genus *Tiarella*, and known by the cultivar name 'Oregon Trail'. The genus *Tiarella* is a member of the family Saxifragaceae.

The new cultivar originated from a planned breeding program as a cross between *Tiarella* 27-04, a proprietary, unreleased trailing *Tiarella* as the seed parent and massed proprietary trailing *Tiarella* as the pollen parent. The exact pollen parent is unknown. Compared to *Tiarella* 'Happy Trails' (U.S. Plant Pat. No. 21,933), the new cultivar has bigger leaves that are more deeply cut.

Compared to *Tiarella* 'Cascade Creeper' (U.S. Plant Pat. No. 21,925), the new cultivar has fewer flowers, smaller leaves, different leaf lobing, and trails more rapidly.

SUMMARY OF THE INVENTION

This plant is uniquely characterized by the following:

1. medium size, palmately-lobed leaves, with the terminal lobe the longest;
2. an extremely good trailing habit;
3. low inflorescence number for a cleaner look;
4. distinct, dark brown markings following the veins; and
5. excellent vigor.

The new variety has been reproduced only by asexual propagation (division and micropropagation). Each of the progeny exhibits identical characteristics to the original plant. Asexual propagation by division and micropropagation using standard techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows *Tiarella* 'Oregon Trail' grown outside in the trial bed in May in Canby, Oreg.

FIG. 2 shows a close up of the foliage in July from plants grown indoors.

DETAILED PLANT DESCRIPTION

The following is a detailed description of the new *Tiarella* cultivar based on observations of one-year-old plants grown together in one gallon containers in a cool greenhouse in March in Canby, Oreg. Canby is Zone 8 on the USDA Hardiness map. Temperatures range from a high of 95 degrees F. in August to an average low of 32 degrees F. in January. Normal rainfall in Canby is 42.8 inches per year. The color descriptions are all based on The Royal Horticultural Society Colour Chart, 5$^{th}$ edition.

Plant:

*Type*.—Herbaceous perennial.
*Hardiness*.—USDA Zones 4 to 9.
*Form*.—Trailing.
*Size*.—108 cm wide and 7.5 cm high from the soil to the top of the foliage.
*Vigor*.—Excellent.
*Roots*.—Fibrous, freely branching, fine, and white in color; roots develop easily from stem cuttings.

Stem:

*Type*.—Decumbent with adventitious roots at the nodes.
*Size*.—Grows to 3 mm wide and 90 cm long.
*Surface*.—Pubescent.
*Internodes*.—2 cm to 7 cm long.
*Color*.—Between Brown 200B and Greyed Purple 187B.

Basal leaves:

*Type*.—Simple.
*Arrangement*.—Rosette.
*Shape*.—Ovate overall.

*Lobing*.—Variable, 7 to 9 deep lobes, terminal lobe the longest, all with secondary lobes.
*Margins*.—Crenate.
*Venation*.—Palmate.
*Apex*.—Acute.
*Base*.—Cordate, sometimes overlapping slightly.
*Blade*.—Grows to 7.5 cm long and 6 cm wide.
*Surface*.—Hispid top and bottom, matte.
*Petiole description*.—5 to 8 cm long and 1.5 mm wide, hirsute, Grey Brown N199B.
*Leaf color*.—Topside, Green N137A with a dark pattern along the veins, Greyed Purple 187A darkening to N186A on older leaves; bottom side Yellow Green 147B with markings Greyed Purple N187A.

Stem leaves:
*Type*.—Simple.
*Arrangement*.—Alternate.
*Shape*.—Ovate overall.
*Lobing*.—Variable, 7 lobes, deeply cleft, the terminal lobe the longest, each lobes with secondary lobes.
*Margins*.—Crenate.
*Venation*.—Palmate.
*Apex*.—Mucronulate.
*Base*.—Cordate, sometimes overlapping.
*Blade*.—Grows to 6.5 cm long and 6 cm wide.
*Surface*.—Hispid top and bottom, matte.
*Petiole description*.—2 to 5 cm long and 1.5 mm wide, hirsute, between Brown 200B and Greyed Purple 187B.
*Leaf color*.—Topside, Green N137A with a dark pattern along the veins, Greyed Purple 187A darkening to N186A on older leaves; bottom side Yellow Green 147B with markings Greyed Purple N187A.

Inflorescence:
*Type*.—Raceme.
*Flower number*.—30 to 40 per raceme.
*Size of inflorescences*.—Grows to 9 cm long and 2 cm wide.
*Number of inflorescences*.—3 in first spring flush.
*Bloom period*.—March to mid June in Canby, Oreg.
*Peduncle*.—Unbranched to 1 branch, grows to 31 cm long and 2.5 cm wide at the base, hispid, between Brown 200B and Greyed Purple 187B.
*Pedicel*.—5 mm long, hispid, between Brown 200B and Greyed Purple 187B.
*Lastingness*.—A raceme blooms for about 3 weeks.

Flower bud:
*Size*.—3 mm deep and 2.5 mm wide.
*Description*.—Ovoid, down facing until open.
*Surface*.—Glandular.
*Color*.—White NN155C.

Flower:
*Type*.—Perfect, actinomorphic, sepals petaloid.
*Shape*.—Rotate.
*Flower size*.—10 mm wide and 5 mm deep including stamens and pistil.
*Corolla*.—5 petals, each 5 mm long and 1 mm wide, lanceolate with a clawed base, margin entire, tip acuminate, glabrous on both sides, White NN155D inside and outside.
*Calyx*.—8 mm wide, 5 sepals, backs glandular, inside glabrous, petaloid, parted almost to the base; lobes obovate, tips obtuse, margins entire to sometimes sparsely serrate, 3 mm long and 1.8 mm wide, White NN155C with tips Yellow Green 147C inside and out.
*Stamens*.—10, conspicuously exerted; filaments 5 mm long, White NN155D; anthers undehisced Orange Red 31C; pollen Yellow Orange 23B.
*Pistil*.—1, White 155C, 5 mm long, ovary 2 mm long, glandular.
*Fragrance*.—None.

Fruit and seed: 6 mm long and 2.5 mm wide, Yellow Green 146C with little seed set; seed Brown 200A, oval, 1.5 mm long.

Pest and disease resistance: This new hybrid shows good mildew tolerance, the main problem for *Tiarella*. No major pest problems. It is susceptible to root weevils, like all *Tiarella*.

I claim:

1. A new and distinct cultivar of *Tiarella* plant herein illustrated and described.

* * * * *

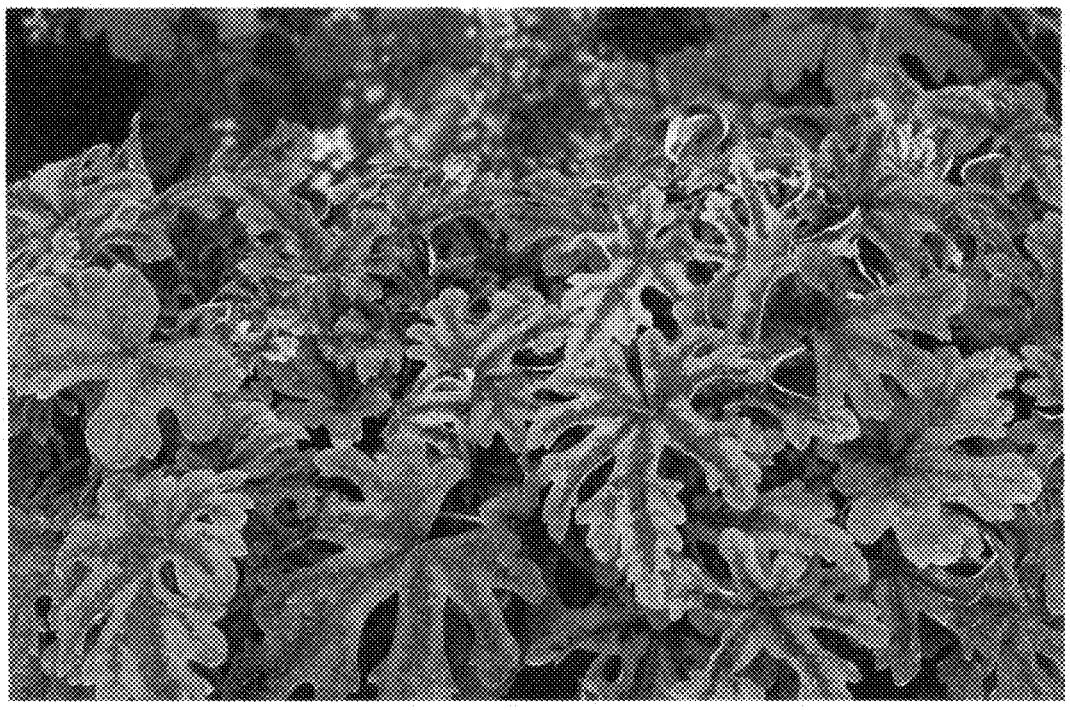

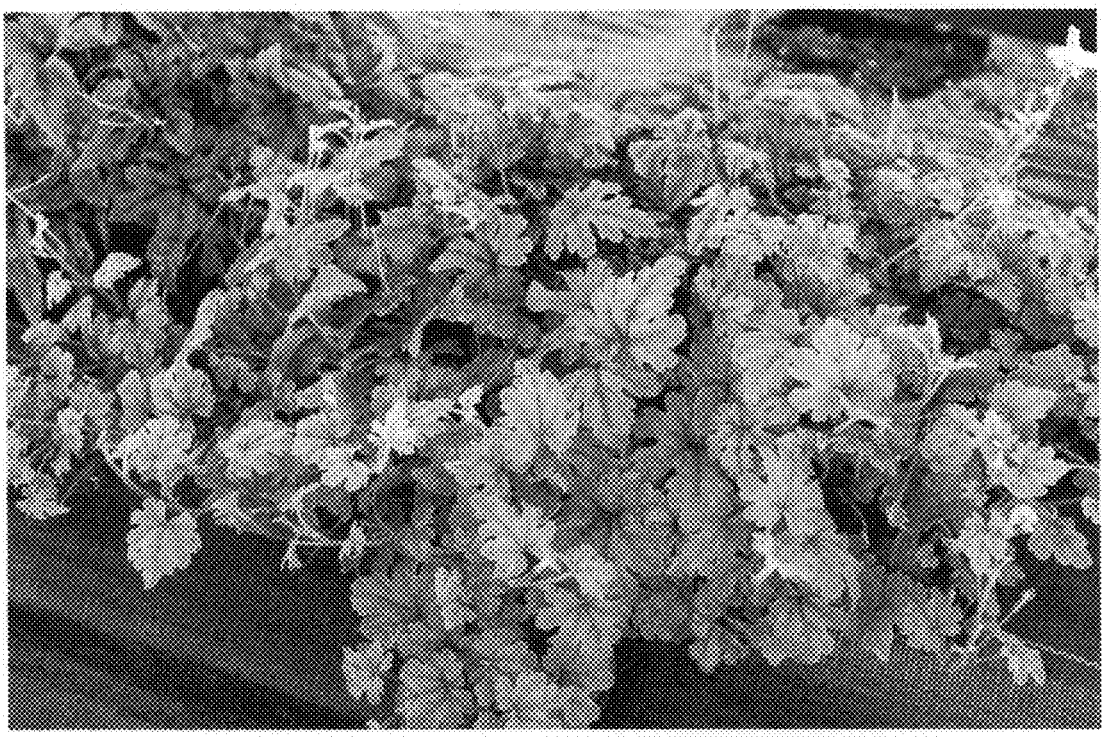
Figure 1 above
Figure 2 below